United States Patent [19]

Seike et al.

[11] Patent Number: 4,653,475
[45] Date of Patent: Mar. 31, 1987

[54] EMBRYO TRANSFERRING APPARATUS ADAPTED FOR ENDOSCOPE

[75] Inventors: Noboru Seike; Masatoshi Teranishi; Minoru Sakai, all of Hokkaido, Japan

[73] Assignee: Snow Brand Milk Products Co., Ltd., Sapporo, Japan

[21] Appl. No.: 705,765

[22] Filed: Feb. 26, 1985

[30] Foreign Application Priority Data

Feb. 28, 1984 [JP] Japan .................................. 59-36850

[51] Int. Cl.⁴ ................................................ A61B 1/00
[52] U.S. Cl. .......................................... 128/4; 604/165
[58] Field of Search .................... 128/3, 4, 5, 6, 7, 8; 604/56, 158, 164, 264, 1, 159, 165

[56] References Cited

U.S. PATENT DOCUMENTS

| 1,127,948 | 2/1915 | Wappler | 128/7 |
| 1,880,551 | 10/1932 | Wappler | 128/7 |
| 4,369,768 | 1/1983 | Vucovic | 128/6 |
| 4,392,485 | 7/1983 | Hiltebrandt | 128/6 |
| 4,538,594 | 9/1985 | Boebel et al. | 128/6 |
| 4,607,619 | 8/1986 | Seike et al. | 128/4 |

FOREIGN PATENT DOCUMENTS

| 7615524 | 10/1976 | Fed. Rep. of Germany | 128/4 |
| 44-22463 | 9/1969 | Japan . | |
| 54-22904 | 8/1979 | Japan . | |
| 2048686 | 12/1980 | United Kingdom | 604/158 |

*Primary Examiner*—William H. Grieb
*Attorney, Agent, or Firm*—Flynn, Thiel, Boutell & Tanis

[57] ABSTRACT

An embryo transferring apparatus adapted for an endoscope comprises: an inner tube extending through an optical visual pipe of the endoscope so as to protrude forward its front end beyond a front end of the optical visual pipe; an outer tube in which the inner tube is inserted slidably to and fro; and an embryo transferring tube movable in the inner tube and extending so as to protrude forward its front end beyond a front end of the inner tube, wherein in the vicinity of the front end of the inner tube is provided a gas discharging opening which is retracted in the outer tube when the latter is moved forward, and is unsheathed from the outer tube when the same is moved backward.

6 Claims, 11 Drawing Figures

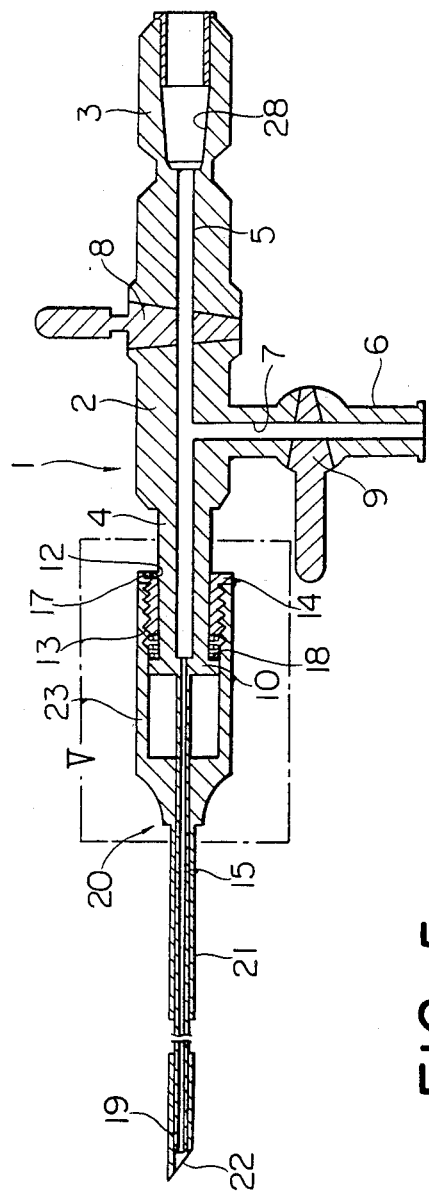
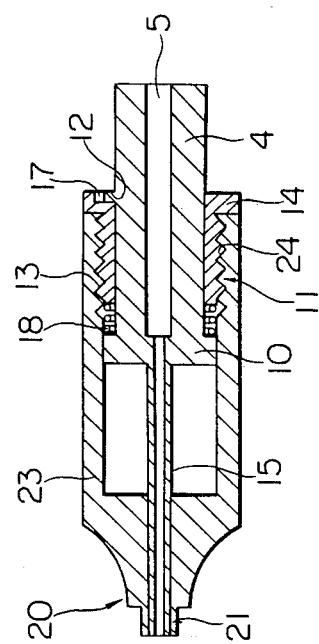
FIG. 4
FIG. 5

U.S. Patent  Mar. 31, 1987  Sheet 3 of 5  4,653,475

EMBRYO TRANSFERRING APPARATUS ADAPTED FOR ENDOSCOPE

BACKGROUND OF THE INVENTION

1. Field of the Invention

The present invention relates to an embryo transferring apparatus for implanting an embryo in a conceptive domestic animal, which apparatus is attached to an endoscope.

2. Description of the Prior Art

There are two methods for transferring the embryo in the conceptive domestic animal, i.e., a surgical operation method and a non-surgical (via Cervix uteri) method. The former having a conceptive ratio of about 70 to 80% is superior in conceptive ratio to the latter having a conceptive ratio of about 30 to 50%. However, the former has its demerits in that it can not be repeated and it takes much time and cost to be performed.

Although the latter can eliminate these demerits of the former, it has a demerit in its poor conceptive ratio as mentioned above.

In order to eliminate the demerits inherent in the above-mentioned methods and to provide an apparatus which enables the transfer to be repeated and to take not much time and cost and further to increase its conceptive ratio, there are provided apparatuses disclosed in Japanese Patent Publication Nos. 22463/1969 and 22904/1979.

However, the apparatus disclosed in the Japanese Patent Publication No. 22463/1969 has demerits in that it is cumbersome in operation and requires a skilled operator since it is necessary to check a uterus by hand inserted in a rectum, which uterus is expanded with a carbon dioxide gas fed fron an installation provided independently of an instrument which has been inserted in a vagina in order to confirm whether a needle point of the instrument is inserted in the uterus so that the operator confirms an accurate position of the needle point to perform an injecting operation of the embryo received in the instrument.

On the other hand, the apparatus disclosed in the Japanese Patent Publication No. 22904/1979 has demerits in that it lacks the accuracy and reliability since the operator can not see directly the uterus, a transfer position therein and a transfer condition therein, though it has merits in that it enables the operator to perform the operation easily and speedily without any assistant help since it has an outer inserting tube in which a piercing tube is slidably inserted and a piercing needle tube is provided therein so as to be projectable from a front end opening of the outer inserting tube, in which piercing needle tube is inserted an embryo injecting tube on which an injecting fine tube having a rounded point is mounted so as to enable the operator to detect a reciprocating movement of the embryo injecting tube by his hand so that he may operate the apparatus by only his manual operation while he confirms the reciprocating movement by his hand, which apparatus is light in weight and therefore portable.

SUMMARY OF THE INVENTION

It is an object of the present invention to provide an embryo transferring apparatus which eliminates the demerits inherent in the conventional type of the embryo transferring apparatus as mentioned above and is easy in its operation so as to not require a skilled operator in use.

The above object of the present invention is achieved by providing an embryo transferring apparatus which is detachably attached to an endoscope in accordance with the present invention, which apparatus has a manipulating terminal provided with a hand pipe from which an inner tube of the transferring apparatus extends forward within an optical visual pipe of the endoscope so that its front end extends forwardly from the front end of the optical visual pipe, which apparatus is provided with: an outer tube member having an outer tube in which the inner tube is inserted, which outer tube member is attached to the hand pipe so as to be movable forwardly and rearwardly; and an embryo injecting member having an injecting tube the front end of which extends forwardly so as to extend from the front end of the inner tube, which injecting member is detachably attached to the hand pipe and is movable within the inner tube. In the vicinity of the front end of the inner tube there is provided a gas discharging opening. When the outer tube member is moved forwardly, the front end of the inner tube is retracted in the outer tube, while when the outer tube is moved backwardly, the gas discharging opening of the inner tube protrudes outwardly from the outer tube. In use, while the operator confirms a front end portion of the uterus and observes an ovary substrate with the use of the endoscope inserted in the vicinity of the uterus, he inserts the outer tube into the optical visual pipe, in which outer tube is inserted the inner tube, the front end of which is retracted in the outer tube, so as to pierce the endometrium. Thereafter, the gas discharging opening of the inner tube is opened in the uterine cavity by moving the outer tube backward so as to inject carbon dioxide gas into the uterine cavity to form a certain space therein. When such a certain space is formed in the uterine cavity, the injecting tube of the embryo injecting member which receives and contains the embryo in its inner tube is inserted in the uterine cavity to transfer the embryo therein. Since the above is the entire operation of the apparatus of the present invention, the operation of the apparatus of the present invention is quite simple and this makes it possible to realize an accurate transfer operation.

It is another object of the present invention to provide an embryo transferring apparatus which performs a transfer of the embryo under aseptic conditions, in which transfer a certain space is formed first in the uterine cavity by injecting the carbon dioxide gas therein, and then the embryo injecting member is attached to the manipulating terminal to perform the transfer while bacteria and the like are prevented from entering the inside of the endoscope and the uterine cavity.

The above another object of the present invention is achieved by an embodiment of the present invention, which embodiment is provided with: a hand pipe; a forward extension extending forwardly from the hand pipe, to which extension an inner tube is attached; a backward extension extending backwardly from the hand pipe and having an inner hole in its inside, in which hole a flange portion provided at the rear end of the embryo injecting member is inserted; a through-hole penetrating the manipulating terminal between these extensions; a gas feeding member attached at right angles to the hand pipe and having an inner hole in its inside, which inner hole communicates with the above through-hole; and cocks for opening and closing the through-hole and the inner hole of the gas feeding member. The inner hole of the gas feeding member is opened only when it is required to feed the gas, and the through-hole is opened only when it is required to attach the embryo injecting member so that these cocks are kept in closed condition always except at the above-mentioned time so as to cut off the inside of the transferring apparatus from communication with the outside world through the through-hole and the inner hole of the gas feeding member to prevent bacteria and the outside atmosphere from entering the inside of the transferring apparatus.

It is yet another object of the present invention to provide an embryo transferring apparatus in which: the inner tube thereof for feeding the gas for forming a certain space in the uterine cavity for performing the transfer of the embryo is kept in a condition in which the gas discharging opening of the inner tube is covered by the outer tube while the inner tube pierces into the organ; and then the inner tube is kept in a condition in which the gas discharging opening of the inner tube is protruded out of the outer tube while the gas is discharged.

The above yet another object of the present invention is achieved by an embodiment of the present invention, in which embodiment the outer tube attached movably to and fro to the forward extension of the hand pipe of the manipulating terminal comprises an enlarged diameter portion at its rear end, which enlarged diameter portion is detachably attached to a sleeve in which the forward extension is slidably inserted, which sleeve has a slit extending longitudinally and a concave portion communicating with the slit at the rear end of the slit and extending in a circumferential direction of the sleeve, in which forward extension is provided a pin which is slidably inserted in the slit of the sleeve, at a front end of which forward extension is formed an annular flange, between which annular flange and a front end of the sleeve a spring is interposed. Namely, when it is required to cover the gas discharging opening of the inner tube by means of the outer tube, the pin provided in the forward extension is engaged with the concave portion of the sleeve to hold the outer tube member in its forward position together with the sleeve against the urging force of the spring, and in case that it is required to protrude the gas discharging opening of the inner tube out of the outer tube, the outer tube member is rotated together with the sleeve relative to the forward extension so as to bring the slit to a position in which the slit is aligned with the pin so that the sleeve or the outer tube member is moved backward by the urging force of the spring while the pin slides in the slit, and therefore it is possible to have the pin engaged with the end face of the slit whereby it is possible to hold the outer tube member in its backward position and to hold the gas discharging opening in its opening position.

BRIEF DESCRIPTION OF THE DRAWINGS

In the drawings:

FIG. 4 is a partially broken away, enlarged, longitudinal sectional view of the transferring apparatus shown in FIG. 1;

FIG. 5 is an enlarged view of a portion encircled by the line V of FIG. 4;

DESCRIPTION OF THE PREFERRED EMBODIMENT

Figure 1:
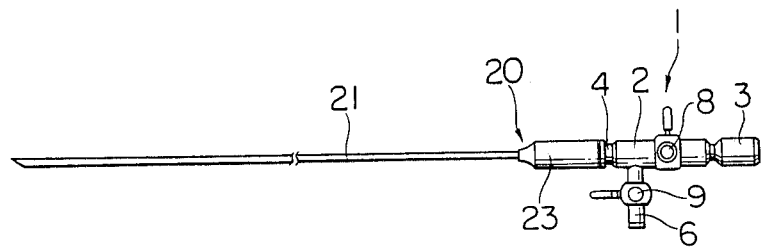
FIG. 1 is a partially broken away side view of the embodiment of the embryo transferring apparatus adapted for the endoscope according to the present invention, in which the embryo injecting member is omitted.
Figure 2:
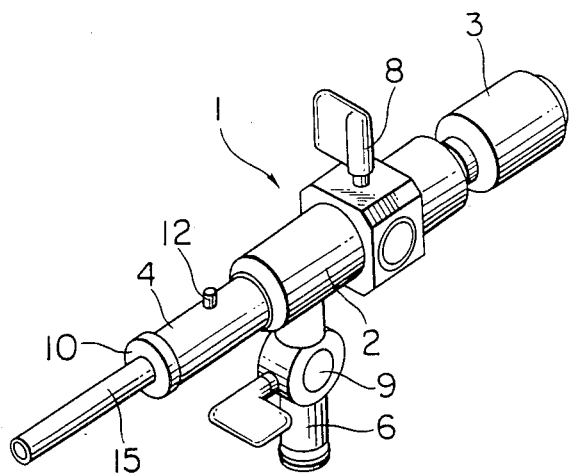
FIG. 2 is a perspective view of the manipulating terminal of the transferring apparatus shown in FIG. 1.
Figure 3:
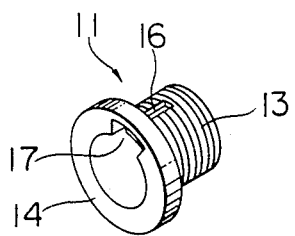
FIG. 3 is a perspective view of the sleeve attached to the forward extension of the hand pipe of the manipulating terminal shown in FIG. 2.

The reference numeral 1 designates a manipulating terminal having a straight hand pipe 2, on the rearward and forward ends of which pipe 2 extensions 3 and 4 are formed, respectively. A through-hole 5 is provided in the manipulating terminal 1 so as to penetrate the same and the extensions 3 and 4 longitudinally. In a rear portion of the extension 4 is provided at right angles to the hand pipe 2 a gas feeding pipe 6 having an inner hole 7 which is connected to the through-hole 5. Further, behind the gas feeding pipe 6, a cock 8 is provided in the hand pipe 2 and another cock 9 is provided in the gas feeding pipe 6 so as to make it possible to open and to close the through-hole 5 and the inner hole 7.

In diameter, the extension 4 is smaller than the hand pipe 2, and the former is provided with an annular flange 10 at its front end, from which flange 10 extends forwrd an inner tube 15 which has a further smaller diameter than that of the extension 4 on an outer peripheral surface of which is provided a pin 12. The extension 4 is slidably inserted in a sleeve 11 which is provided with: a screw portion 13 on an outer periphery of which a male screw is formed; and an annular flange 14 adjacent thereto. Between a middle portion of the screw portion 13 and an end face of the annular flange 14 is longitudinally provided a slit 16 communicating with a circumferential concave portion 17 which is formed in the end face of the annular flange 14. A spring 18 is interposed between the annular flange 10 and the sleeve 11 to urge the sleeve 11 always toward the hand pipe 2. In the implanting apparatus of the present invention, when not in use, the sleeve 11 is positioned spaced from the hand pipe 2 as shown in FIGS. 4 and 5 and the pin 12 of the extension 4 engages with a side wall of the concave portion 17 of the annular flange 14 in a longitudinal direction of the sleeve 11 whereby the spring 18 is compressed. In the vicinity of the front end of the inner tube 15 is laterally provided a gas discharging opening 19.

The reference numeral 20 designates an outer tube member having an outer tube 21 in which the inner tube 15 is inserted. In a front end of the outer tube 21 is provided a slant face portion 22, and to a rear end of the outer tube 21 is attached an enlarged diameter tube portion 23 in an inner surface of which is provided a female screw 24 which is meshed with the male screw of the screw portion 13.

Figure 6:
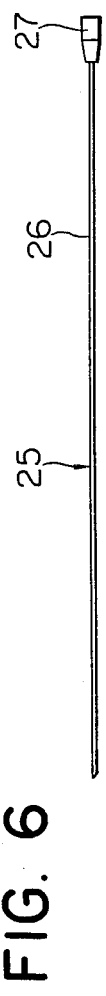
FIG. 6 is a front view of the embryo injecting member which is inserted in the transferring apparatus shown in FIG. 1 in use.

In FIG. 6 is shown the fertilized ovum injecting member 25 which comprises an injecting tube 26 inserted slidably in the inner tube 15, and a flange portion 27 attached to a base end thereof.

Figure 9:
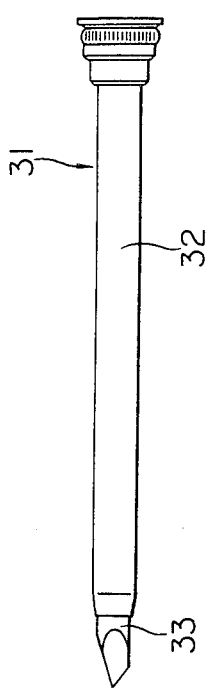
FIG. 9 is a front view of the conventional trocar which is used first in the transfer operation of the embryo with the use of the embryo transferring apparatus of the present invention.

In use, the conventional trocar 31 as shown in FIG. 9 pierces first into the organ and then an inner needle 33 is drawn out of an outer tube 32 while the outer tube 32 is held as it is in that piercing place.

Figure 10:
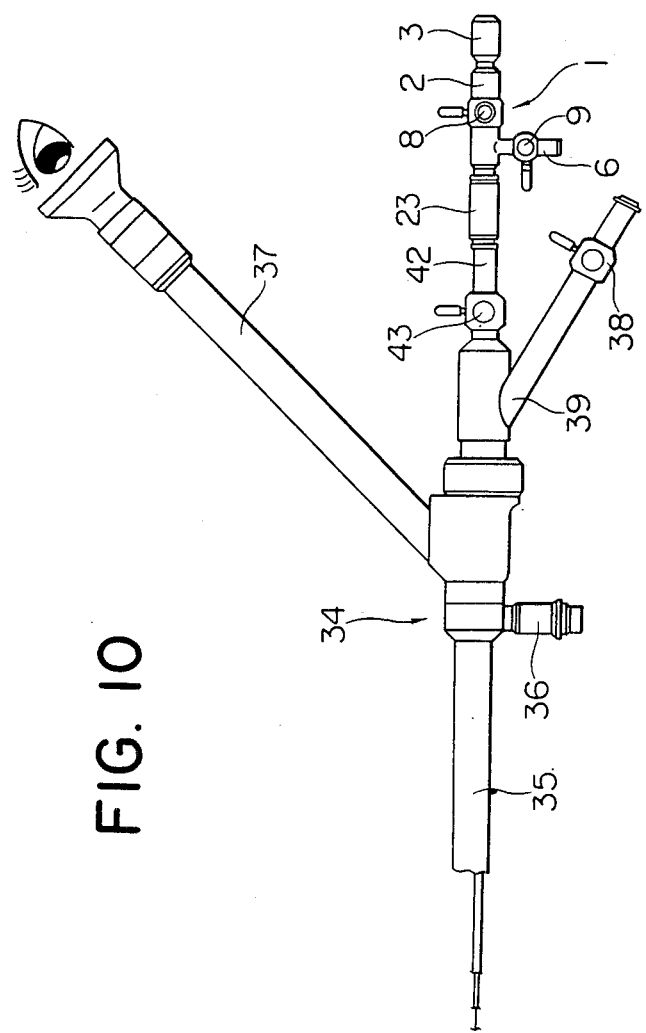
FIG. 10 is a front view of the transferring apparatus of the present invention, which is in an operative condition together with the conventional endoscope to which is attached the transferring apparatus of the present invention in the transfer operation of the embryo.

Then, into this outer tube 32 the conventional endoscope 34 as shown in FIG. 10 is inserted and a lamp of a light source attached to a light-guide mounting member 36 is turned on whereby it is possible to confirm visually a front end portion of the uterus through an eyepiece member 37 and also possible to observe an ovary substrate.

Now, the embryo is received in the embryo injecting member 25 and retained therein.

Figure 11:
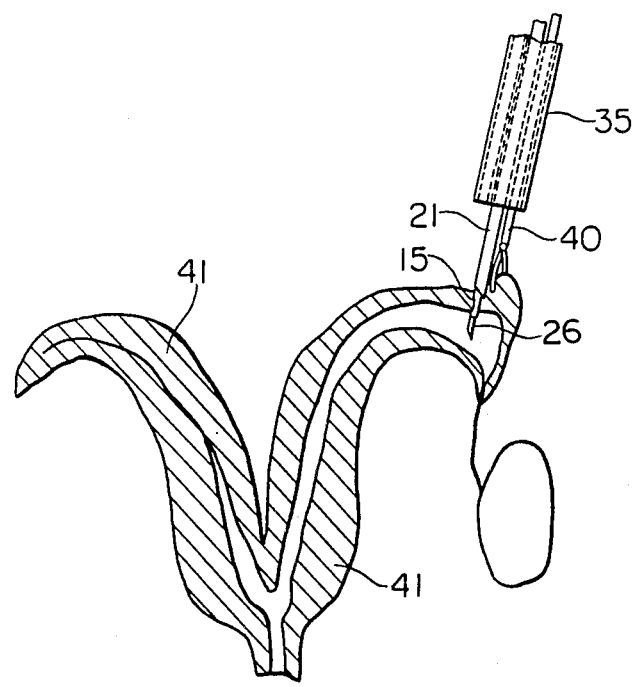
FIG. 11 is a view showing the condition of the transfer operation of the embryo by means of the embryo transferring apparatus of the present invention.

After that, the cock 38 is opened to introduce a handling forceps 40 from a handling forceps inserting member 39 into the uterine cavity so as to enable the operator to catch a portion of the uterus through the forceps 40 and to keep it at a certain position as shown in FIG. 11.

Then, cock 43 for an operative instrument inserting member 42 is opened to insert into the same the outer tube 21 of the outer tube member 20 of the transferring apparatus in a condition shown in FIG. 4, except that the cocks 8 and 9 are closed. At this time, the outer tube member 20 is positioned in its forward position to compress the spring 18 as mentioned above while the front end of the inner tube 15 is covered by the front end of the outer tube 21 to retract the gas discharging opening 19 of the inner tube 15 into the outer tube 21. This condition is maintained by an engagement between the pin 12 and the wall face of the concave portion 17, and in this condition the endometrium is pierced by the outer tube 21 with the use of the slant face portion 22 of its front point whereby the outer tube 21 is held in this pierced position of the endometrium.

Figure 7:
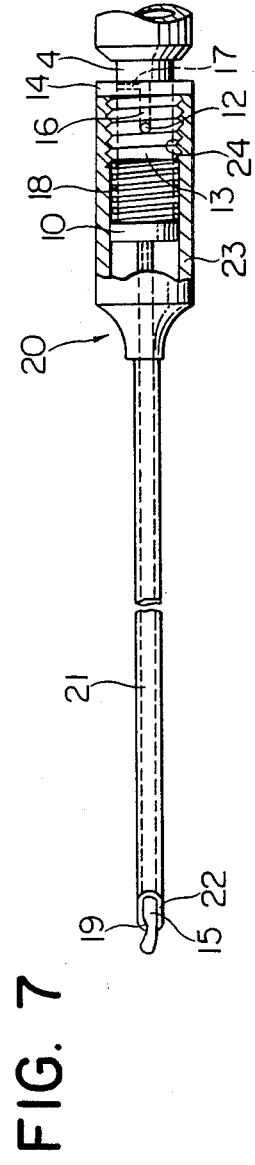
FIG. 7 is a view similar to FIG. 4 except that the outer tube member is moved into another position.

Now, the operator rotates the sleeve 11 with the use of the enlarged diameter tube portion 23 of the outer tube member 20 to a position in which the slit 16 of the sleeve 11 is aligned with the pin 12, in which position the sleeve 11 is moved by the spring 18 to drive the pin 12 in the slit so as to move the sleeve 11 or the outer tube member 20 to its backward position shown in FIG. 7, whereby the gas discharging opening 19 of the inner tube 15 is exposed to the outside world and at the same time the gas discharging opening 19 passes the endometrium to reach into the uterine cavity. Then, the cock 9 is opened to inject the carbon dioxide gas into the uterus from the rear end of the extension 3 through the through-hole 5 from the gas feeding pipe 6 so as to form a certain space in the uterus as shown in FIG. 11, and thereafter the cock 9 is closed.

Figure 8:
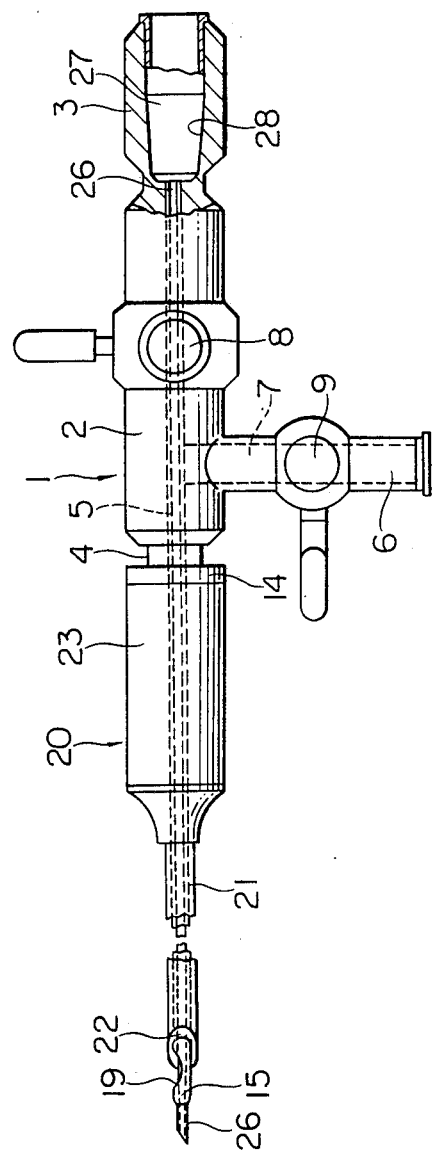
FIG. 8 is a partially broken away, enlarged, front view of the embodiment shown in FIG. 1, in the transfer operation of the embryo.

After that, the cock 8 is opened and into the rear end of the extension 3 is inserted the injecting tube 26 of the injecting member 25 holding the embryo therein to seat its flange portion 27 on the end face of the inner hole 28 so that the front end of the injecting tube 26 is protruded forward beyond the front end of the inner tube 15 as shown in FIG. 8 to communicate with the cavity of the uterus 41 as shown in FIG. 11, whereby the embryo is transferred in the uterine cavity. After completion of the feeding operation of the carbon dioxide gas into the uterine cavity and till completion of the transfer operation of the embryo, the cocks 8, 9 are closed to prevent the transfer path of the embryo from being contaminated by the bacteria and the like.

Although a particular preferred embodiment of the present invention has been disclosed in detail for illustrative purposes, it will be recognized that variations or modifications of the disclosed transferring apparatus, including the rearrangement of parts, lie within the scope of the present invention.

What is claimed is:

1. An endoscope apparatus adapted for transferring an embryo to the uterus of a conceptive animal, comprising:

an endoscope comprising an elongated optical visual pipe having a front end, an eyepiece member for viewing the uterus of the conceptive animal, a light guide mounting member adapted to receive a lamp for illuminating the uterus, an operative instrument inserting member and a handling forceps insertion member;

an embryo transferring apparatus detachably attached to said endoscope, said embryo transferring apparatus comprising a manipulating terminal having a hand pipe and an inner tube extending forwardly therefrom and extending through said optical visual pipe of said endoscope so that the front end of said inner tube protrudes beyond the front end of said optical visual pipe, said inner tube having a gas discharging opening located close to the front end of said inner tube;

an outer tube member slidably mounted on said hand pipe for movement between forward and rearward positions relative to said hand pipe, said outer tube member having an outer tube projecting forwardly therefrom, said inner tube extending forwardly through the inside of said outer tube;

an embryo transferring member detachably attached to said hand pipe, said embryo transferring member comprising an injecting tube which extends forwardly through the inside of said inner tube so that its front end can project beyond the front end of said inner tube, said outer tube member being constructed and arranged so that when it is in its forward position relative to said hand pipe, the front end of said inner tube is disposed within and is covered by said outer tube member and when said outer tube member is in its rearward position relative to said hand pipe, said gas discharging opening is uncovered so that gas can be discharged therefrom;

and a handling forceps extending through said handling forceps insertion member, said handling forceps extending forwardly through said optical visual pipe of said endoscope, protruding beyond the front end of said optical visual pipe and being located close to said outer tube member so that the handling forceps can grip a portion of the uterus close to the location at which said injecting tube in inserted into the uterus.

2. The apparatus as set forth in claim 1 in which said manipulating terminal comprises a forward extension extending forwardly from the front end of said hand pipe, said inner tube being attached to and extending forwardly from said forward extension, said manipulating terminal having a backward extension extending backwardly from the rear end of said hand pipe, the rear end of said backward extension having an internal hole, said manipulating terminal having a through hole extending lengthwise therethrough from said internal hole of said backward extension through the front end of said forward extension; a gas-feeding member extending at a right angle to said hand pipe and having an internal gas-feeding passageway that communicates with said through hole; a first cock for opening and closing said gas-feeding passageway and a second cock for opening and closing said through hole; said embryo transferring member having a flange portion seated in said internal hole in said backward extension.

3. The apparatus as set forth in claim 2 wherein said outer tube member comprises an enlarged diameter tube portion attached to the rear end of said outer tube; a sleeve detachably attached to said enlarged diameter tube portion, said forward extension of said manipulating terminal being inserted in said sleeve for sliding movement with respect thereto, said sleeve having a longitudinally extending slit and an arcuate, circumferentially extending recess portion provided in the rear end face of said sleeve and communicating with said slit, said forward extension having an outwardly projecting pin which is slidably disposed in said slit and is movable into said recess portion when said outer tube member is in its forward position, said forward extension of said manipulating terminal having an annular flange at the front end thereof, which flange is disposed inside said enlarged diameter tube portion and in opposed relation to the front end of said sleeve; and a compression spring interposed between said front end of said sleeve and said flange.

4. The apparatus as claimed in claim 3 wherein said enlarged diameter tube portion is detachably attached to said sleeve by a threaded connection.

5. The apparatus as set forth in claim 1 wherein said manipulating terminal comprises a forward extension extending forwardly from the front end of said hand pipe, said outer tube member comprises an enlarged diameter tube portion attached to the rear end of said outer tube; a sleeve detachably attached to said enlarged diameter tube portion, said forward extension of said manipulating terminal being inserted in said sleeve for sliding movement with respect thereto, said sleeve having a longitudinally extending slit and an arcuate, circumferentially extending recess portion provided in the rear end face of said sleeve and communicating with said slit, said forward extension having an outwardly projecting pin which is slidably disposed in said slit and is movable into said recess portion when said outer tube member is in its forward position, said forward extension of said manipulating terminal having an annular flange at the front end thereof, which flange is disposed inside said enlarged diameter tube portion and in opposed relation to the front end of said sleeve; and a compression spring interposed between said front end of said sleeve and said flange.

6. The apparatus as claimed in claim 5 wherein said enlarged diameter tube portion is detachably attached to said sleeve by a threaded connection.

* * * * *